(12) United States Patent
Oh et al.

(10) Patent No.: US 7,374,930 B2
(45) Date of Patent: May 20, 2008

(54) GLP-1 GENE DELIVERY FOR THE TREATMENT OF TYPE 2 DIABETES

(75) Inventors: Seungjoon Oh, Seoul (KR); Minhyung Lee, Seoul (KR); Kyungsoo Ko, Seoul (KR)

(73) Assignee: Expression Genetics, Inc., Huntsville, AL (US)

( * ) Notice: Subject to any disclaimer, the term of this patent is extended or adjusted under 35 U.S.C. 154(b) by 796 days.

(21) Appl. No.: 10/153,470

(22) Filed: May 21, 2002

(65) Prior Publication Data

US 2003/0220274 A1    Nov. 27, 2003

(51) Int. Cl.
*C12N 15/63*    (2006.01)

(52) U.S. Cl. .................................. 435/320.1; 536/23.1

(58) Field of Classification Search ................ None
See application file for complete search history.

(56) References Cited

U.S. PATENT DOCUMENTS

| | | | |
|---|---|---|---|
| 5,545,618 A | 8/1996 | Buckley et al. | |
| 5,614,492 A | 3/1997 | Habener | |
| 5,958,909 A | 9/1999 | Habener | |
| 5,990,077 A | 11/1999 | Drucker | |
| 5,994,127 A * | 11/1999 | Selden et al. | 435/325 |
| 6,048,724 A | 4/2000 | Selden et al. | |
| 6,162,907 A | 12/2000 | Habener | |
| 6,191,102 B1 | 2/2001 | DiMarchi | |
| 6,217,912 B1 | 4/2001 | Park et al. | |
| 6,258,789 B1 | 7/2001 | German | |

FOREIGN PATENT DOCUMENTS

WO    WO 00/23602    *    4/2000

OTHER PUBLICATIONS

Miyazaki et al (Gene, 1989, vol. 79, pp. 269-277).*
F. Mauvais-Jarvis, et al *Therapeutic Perspectives for Type 2 Diabetes Mellitus: Molecular and Clinical Insights*, Diabetes Metab (Paris) 2001, 27, 415-423.
Q. Xiao, et al *Biological Activities of Glucagon-Like Peptide-1 Analogues in Vitro and in Vivo*, Departments of Medicine and Physiology, University of Toronto, Dec. 11, 2000.
Yihong Wang, et al, *Glucagon-like Peptide-1 Can Reverse the Age-related Decline in Glucose Tolerance in Rats*, The Journal of Clinical Investigation, vol. 99, No. 12, Jun. 1997, 2883-2889.
David G. Parkes, et al, *Insulinotropic Actions of Exendin-4 and Glucagon-Like Peptide-1 In Vivo and In Vitro*, Metabolism, vol. 50, No. 5 (May 2001), pp. 583-589.
N Dachicourt, et al *Glucagon-Like Peptide-1 (7-36)-amide confers glucose sensitivity to previously glucose-incompetent β-cells in diabetic rats: in vivo and in vitro studies*, Journal of Endocrinology (1997) 155, 369-376.

(Continued)

*Primary Examiner*—Celine Qian
(74) *Attorney, Agent, or Firm*—Thorpe North & Western LLP (57) ABSTRACT

This patent discloses compositions and methods of use thereof to normalize the blood glucose levels of patients with type 2 diabetes. It relates particularly to a plasmid comprising a chicken β actin promoter and enhancer; a modified GLP-1 (7-37) cDNA (pβGLP1), carrying a furin cleavage site, which is constructed and delivered into a cell for the expression of active GLP-1.

1 Claim, 5 Drawing Sheets

Plasmid map of pβGLP1

OTHER PUBLICATIONS

Francis C. Lynn, et al, *Defective Glucose-Dependent Insulinotropic Polypeptide Receptor Expression in Diabetic Fatty Zucker Rats* Diabetes, vol. 50, May 2001.

Seamus K, Sreenan, et al, *Glucagon-Like Peptide-1 Stimulates Insulin Secretion by a Ca2+-Independent Mechanism in Zucker Diabetic Fatty Rat Islets of Langerhans* Mechanism, vol. 49, No. 12 (Dec. 2000), pp. 1579-1587.

Philip J. Larsen, et al, *Systemic Administration of the Long-Acting GLP-1 Derivative NN2211 Induces Lasting and Reversible Weight Loss in Both Normal and Obese Rats*, Diabetes, vol. 50, Nov. 2001.

Laurie Baggio, et al, *Glucagon-Like Peptide-1, But Not Glucose-Dependent Insulinotropic Peptide, Regulates Fasting Glycemia and Nonenteral Glucose Clearance in Mice*, Endocrinology, vol. 141, No. 10, 2002.

Diane M. Hargrove, et al. *Glucose-Dependent Actiopn of Glucagon-Like Peptide-1 (7-37) In Vivo During Short- or Long-Term Administration*, Metabolism, vol. 44, No. 9 (Sep. 1995), pp. 1231-1237.

Lone Pridal, et al *Absorption of Glucagon-like Peptide-1 Can Be Protracted by Zinc or Protamine*, International Journal of Pharmaceutics 136 (1996) 53-59.

Daniel J. Drucker, *Minireview: The Glucagon-Like Peptides*, Endocrinology, vol. 142, No. 2, 2001.

Riccardo Perfetti, et al, *Glucagon-like Peptide-1: a Major Regulator of Pancreatic β-cell Function*, European Journal of Endocrinology (2000) 143 717o-725.

Unger, R. H., Eisentraut AM: Entero-insular axis, *Arch Intern Med* 123:261-266, 1969.

Holst JJ: Glucagonlike peptide 1: a newly discovered gastrointestinal hormone. *Gastroenterology* 107:1848-1855, 1994.

Hauck MA. Heimesaat MN, Orskov C, Holst JJ, Ebert R, Creutzfeldt W: Preserved incretin activity of glucagon-like peptide 1 [7-36 amide] but not of synthetic human gastric inhibitory polypeptide in patients with type-2 diabetes mellitus. *J Clin Invest* 91:301-307, 1993.

Fehmann HC, Goke R, Goke B: Cell and molecular biology of the incretin hormones glucagon-like peptide-1 and glucose-dependent insulin releasing polypeptide. *Endocr Rev* 16:390-410, 1995.

Nauck MA, Sauerwald A, Ritzel R, Holst JJ, Schmiegel W: Influence of glucagon-like peptide 1 on fasting glycemia in type 2 diabetic patients treated with insulin after sulfonylurea secondary failure. *Diabetes Care* 21:1925-1931, 1998.

Rachman J, Barrow BA, Levy JC, Turner RC: Near-normalisation of diurnal glucose concentrations by continuous administration of glucagono-like peptide-1 (GLP-1) in subjects with NIDDM. *Diabetologia* 40:205-211, 1997.

Szayna M, Doiyle ME, Betkey JA, Holloway HW, Spencer RG, Greig NH, Egan JM: Exendin-4 decelerates food intake, weight gain, and fat deposition in Zucker rate. *Endocrinology* 141:1936-1941, 2000.

DeFronzo, R.A., Bonadonna, Riccardo, C., and Ferrannini, Eleuterio: Pathogenesis of NIDDM: A Precarious Balance between Insulin Action and Insulin Secretion. *International Textbook of Diabetes Mellitus*, pp. 569-619, 1992.

Suh, W., et al. An Angiogenic, Endothelial-Cell-Targeted Polymeric Gene Carrier. Nov. 2002. vol. 6, No. 5, pp. 664-672.

Mark Gutniak, M.D., et al., *Antidiabetogenic Effect of Glucagon-Like Peptide-1 (7-36)amide in Normal Subjects and Patients with Diabetes Mellitus*. The New England Journal of Medicine, May 14, 1992.

David M. Nathan, M.D., et al, *Insulinotropic Action of Glucagonlike Peptide-1-(7-37) in Diabetic and Nondiabetic Subjects*. Diabetes Care, vol. 15, No. 2, Feb. 1992.

M. A. Nauck, et al, *Normalization of Fasting Hyperglycaemia by Exogenous Glucagon-Like Peptide 1 (7-36 amide) in Type 2 (non-insulin-dependent) diabetic Patients*, Diabetologia (1993) 36: 741-744.

Mark K. Gutniak, M.D., et al, *Potential Therapeutic Levels of Glucagon-Like Peptide 1 Achieved in Humans by a Buccal Tablet*, Diabetic Care, vol. 19, No. 8, Aug. 1996.

J F. Todd, et al. *Glucagton-like Peptide-1 (GLP-1) a trial of treatment in Non-insulin Dependent Diabetes Mellitus*, European Journal of Clinical Investigation (1997) 27, 533-536.

Diane M. Hargrove, et al, *Glucose-Dependent Action of Glucagon-Like Peptide-1 (7-37) In Vivo During Short- or Long-Term Administration*, Metabolism, vol. 44, No. 9 (Sep. 1995), pp. 1231-1237.

Mark K. Gutniak, M D. et al, *GLP-1 Tablet in Type 2 Diabetes in Fasting and Postprandial Conditions*, Diabetes Care, vol. 20, No. 12, Dec. 1997.

Jens Larsen, M.D., et al. *Glucagon-Like Peptide-1 Infusion Must Be Maintained for 24 h/day to Obtain Acceptable Glyce3mia in Type 2 Diabetic Patients Who Are Poorly Controlled on Sulphonylurea Treatment*, Diabetes Care, vol. 24, No. 8, Aug. 2001.

Tina Vilsboll, et al, *Reduced Postprandial Concentrations of Intact Biologically Active Glucagon-Like Peptide 1 in Type 2 Diabetic Patients*, Diabetes, vol. 50, Mar. 2001.

Tina Visbol, et al, *Evaluation of β-Cell Secretory Capacity Using Glucagon-Like Peptide 1*, Diabetes Care, vol. 23, No. 6, Jun. 1, 2000.

Robert Ritzel, et al, *Glucagon-Like Peptide 1 Increases Secretory Burst Masds of Pulsatile Insulin Secretion in Patients With Type 2 Diabetes and Impaired Glucose Tolerance*, Diabetes. vol. 50, Apr. 2001.

Adrian Vella, et al. *Effect of Glucagon-Like Peptide-1 (7-36)-Amide on Initial Splanchnic Glu8cose Uptake and Insulin Action in Humans With Type 1 Diabetes*, Diabetes. vol. 50, Mar. 2001.

T. Vilsboll, et al, *No Reactive Hypoglycaemia in Type 2 Diabetic Patients After Subcutaneous Administration of GLP-1 and Intravenous Glucose*, 2001 Diabetes UK. Diabetic Medicine, 18, 144-149.

M. K. Gutniak, et al, *Antidiabetogenic Action of Glucagon-Like Peptide-1 Related to Administration Relative to Meal Intake in Subjects with Type 2 Diabetes*, Journal of Internal Medicine 2001: 250: 81-87.

Adrian Vella, et al. *Effect of Glucagon-Like Peptide-1 (7-36)-Amide on Initial Splanchnic Glucose Uptake and Insulin Action in Humans With Type 1 Diabetes*, Diabetes, vol. 50, Mar. 2001.

Tina Vilsboll, et al. *Evaluation of β-Cell Secretary Capacity Using Glucagon-Like Peptide 1*, Diabetes Care, vol. 23, No. 6, Jun. 2000.

C. B. Juhl, et al. *Short-term Treatment with GLP-1 Increases Pulsatile Insulin Secretion in Type II Diabetes with No Effect On Orderliness*, Diabetologia (2000) 43: 583-588.

C. Hedetoft, et al. *Effect of Glucagon-Like Peptide 1 (7-36) Amide in Insulin-Treated Patients with Diabetes Mellitus Secondary to Chronic Pancreatitis*, Pancreas vol. 20, No. 1, pp. 25-31, 2000.

E. Mannucci, et al. *Glucagon-Like Peptide (GLP)-1 and Leptin Concentrations in Obese Patients with Type 2 Diabetes Mellitus*, 2000 Diabetes UK. Diabetic Medicine, 17, 713-719.

Adrian Vella, et al, *Effect of Glucagon-Like Peptide 1 (7-36) Amide on Glucose Effectiveness and Insulin Action in People with Typ4e 2 Diabetes*, Diabetes, vol. 49, Apr. 2000.

Adrian Vella, et al. *Effect of Glucagon-Like Peptide 1 (7-36) Amide on Glucose Effectiveness and Insulin Action in People with Type 2 Diabetes*, Diabetes, vol. 49, Apr. 2000.

C. B. Juhl, et al, *Short-term treatment with GLP-1 Increases Pulsatile Insulin Secretion in Type II Diabetes with No Effect on Orderliness*, Diabetologia (2000) 43: 583-588.

\* cited by examiner

Fig. 1. Plasmid map of pβGLP1

Fig. 2A. RT-PCR results of transfected HepG2 cells

Fig. 2B. GLP-1 production of transfected HepG2 cells

Fig. 3. Insulin secretion of co-cultured islets with pβGLP1 transfected HepG2 cells Fig 4. Therapeutic effect of PAGA /pβGLP1 complex in ZDF rats

SEQUENCE LISTING

<160> NUMBER OF SEQ ID NOS: 5

<210> SEQ ID NO 1
<211> LENGTH: 1201
<212> TYPE: DNA
<213> ORGANISM: chicken
<220> FEATURE:
<221> NAME/KEY: promoter and enhancer
<222> LOCATION: 881, 905, 942, 964, 1043
<223> OTHER INFORMATION: n represents a, t, c, or g.

<400> SEQUENCE: 1

```
agatcttcaa tattggccat tagccatatt attcattggt tatatagcat              50
aaatcaatat tggctattgg ccattgcata cgttgtatct atatcataat             100
atgtacattt atattggctc atgtccaata tgaccgccat gttggcattg             150
attattgact agttattaat agtaatcaat tacggggtca ttagttcata             200
gcccatatat ggagttccgc gttacataac ttacggtaaa tggcccgcct             250
ggctgaccgc ccaacgaccc ccgcccattg acgtcaataa tgacgtatgt             300
tcccatagta acgccaatag ggcatttcca ttgacgtcaa tgggtggagt             350
atttacggta aactgcccac ttggcagtac atcaagtgta tcatatgcca             400
agtccgcccc ctattgacgt caatgacggt aaatggcccg cctggcatta             450
tgcccagtac atgaccttac gggactttcc tacttggcag tacatctacg             500
tattagtcat cgctattacc atggtgatgc ggttttggca gtacaccaag             550
ggcgggatag cggtttgact cacggggatt ccaagtctc cacccattg               600
acgtcaatgg gagtttgttt tggcaccaaa atcaacggga ctttccaaaa             650
tgtcgtaata accccgcccc gttgacgcaa atgggcggta ggcgtgtacg             700
gtgggaggtc tatataagca gagctcgttt agtgaaccgt cagatcacta             750
gaagctttat gcggtagtt tatcacagtt aaattgctaa cgcagtcagt              800
gcttctgaca caacagtctc gaacttaagc tgcagaagtt ggtcgtgagg             850
cactgggcag gtaagtatca aggttacaag ncaggtttaa ggagaccaat             900
agaancttgg gcttgtcgag acagagaaga ctcttgcgtt tntgataggc             950
acctattggt cttnctgaca tccactttgc ctttctctcc acaggtgtcc            1000
actcccagtt caattacagc tcttaggcta gagtacttaa tangactcac            1050
tataggctag cctcgagaat tcacgcgtgg taccatgcgt caacgtcgtc            1100
atgctgaagg gacctttacc agtgatgtaa gttcttattt ggaaggccaa            1150
gctgccaagg aattcattgc ttggctggtg aaaggccgag gatagtctag            1200
a                                                                 1201
```

<210> SEQ ID NO 2
<211> LENGTH: 4120
<212> TYPE: DNA
<213> ORGANISM: chicken
<220> FEATURE:
<221> NAME/KEY: promoter and enhancer
<222> LOCATION: 881, 905, 942, 964, 1043
<223> OTHER INFORMATION: n represents a, t, c, or g.

<400> SEQUENCE: 2

```
agatcttcaa tattggccat tagccatatt attcattggt tatatagcat              50
```

-continued

| | |
|---|---|
| aaatcaatat tggctattgg ccattgcata cgttgtatct atatcataat | 100 |
| atgtacattt atattggctc atgtccaata tgaccgccat gttggcattg | 150 |
| attattgact agttattaat agtaatcaat tacggggtca ttagttcata | 200 |
| gcccatatat ggagttccgc gttacataac ttacggtaaa tggcccgcct | 250 |
| ggctgaccgc ccaacgaccc ccgcccattg acgtcaataa tgacgtatgt | 300 |
| tcccatagta acgccaatag ggcatttcca ttgacgtcaa tgggtggagt | 350 |
| atttacggta aactgcccac ttggcagtac atcaagtgta tcatatgcca | 400 |
| agtccgcccc ctattgacgt caatgacggt aaatggcccg cctggcatta | 450 |
| tgcccagtac atgaccttac gggactttcc tacttggcag tacatctacg | 500 |
| tattagtcat cgctattacc atggtgatgc ggttttggca gtacaccaag | 550 |
| ggcgggatag cggtttgact cacggggatt ccaagtctc cacccattg | 600 |
| acgtcaatgg gagtttgttt tggcaccaaa atcaacggga ctttccaaaa | 650 |
| tgtcgtaata accccgcccc gttgacgcaa atgggcggta ggcgtgtacg | 700 |
| gtgggaggtc tatataagca gagctcgttt agtgaaccgt cagatcacta | 750 |
| gaagctttat tgcggtagtt tatcacagtt aaattgctaa cgcagtcagt | 800 |
| gcttctgaca caacagtctc gaacttaagc tgcagaagtt ggtcgtgagg | 850 |
| cactgggcag gtaagtatca aggttacaag ncaggtttaa ggagaccaat | 900 |
| agaancttgg gcttgtcgag acagagaaga ctcttgcgtt tntgataggc | 950 |
| acctattggt cttnctgaca tccactttgc ctttctctcc acaggtgtcc | 1000 |
| actcccagtt caattacagc tcttaggcta gagtacttaa tangactcac | 1050 |
| tataggctag cctcgagaat tcacgcgtgg taccatgcgt caacgtcgtc | 1100 |
| atgctgaagg gacctttacc agtgatgtaa gttcttattt ggaaggccaa | 1150 |
| gctgccaagg aattcattgc ttggctggtg aaaggccgag gatagtctag | 1200 |
| atagagtcga cccgggcggc cgcttcgagc agacatgata agatacattg | 1250 |
| atgagtttgg acaaaccaca actagaatgc agtgaaaaaa atgctttatt | 1300 |
| tgtgaaattt gtgatgctat tgctttattt gtaaccatta taagctgcaa | 1350 |
| taaacaagtt aacaacaaca attgcattca ttttatgttt caggttcagg | 1400 |
| gggagatgtg gaggttttt taaagcaagt aaaacctcta caaatgtggt | 1450 |
| aaaatcgata aggatccggg ctggcgtaat agcgaagagg cccgcaccga | 1500 |
| tcgcccttcc caacagttgc gcagcctgaa tggcgaatgg acgcgccctg | 1550 |
| tagcggcgca ttaagcgcgg cgggtgtggt ggttacgcgc agcgtgaccg | 1600 |
| ctacacttgc cagcgcccta gcgcccgctc ctttcgcttt cttcccttcc | 1650 |
| tttctcgcca cgttcgccgg ctttccccgt caagctctaa atcggggct | 1700 |
| cccttagg ttccgattta gtgctttacg gcacctcgac cccaaaaaac | 1750 |
| ttgattaggg tgatggttca cgtagtgggc catcgccctg atagacggtt | 1800 |
| tttcgccctt tgacgttgga gtccacgttc tttaatagtg gactcttgtt | 1850 |
| ccaaactgga acaacactca accctatctc ggtctattct tttgatttat | 1900 |
| aagggatttt gccgatttcg gcctattggt taaaaatga gctgatttaa | 1950 |
| caaaaattta acgcgaattt taacaaaata ttaacgctta caatttcctg | 2000 |

```
atgcggtatt ttctccttac gcatctgtgc ggtatttcac accgcatatg      2050
gtgcactctc agtacaatct gctctgatgc cgcatagtta agccagcccc      2100
gacacccgcc aacacccgct gacgcgccct gacgggcttg tctgctcccg      2150
gcatccgctt acagacaagc tgtgaccgtc tccgggagct gcatgtgtca      2200
gaggttttca ccgtcatcac cgaaacgcgc gagacgaaag ggcctcgtga      2250
tacgcctatt tttataggtt aatgtcatga taataatggt ttcttagacg      2300
tcaggtggca cttttcgggg aaatgtgcgc ggaaccccta tttgtttatt      2350
tttctaaata cattcaaata tgtatccgct catgagacaa taaccctgat      2400
aaatgcttca ataatattga aaaggaaga gtatgagtat tcaacatttc       2450
cgtgtcgccc ttattccctt ttttgcggca ttttgccttc ctgttttgc       2500
tcacccagaa acgctggtga aagtaaaaga tgctgaagat cagttgggtg      2550
cacgagtggg ttacatcgaa ctggatctca acagcggtaa gatccttgag      2600
agttttcgcc ccgaagaacg ttttccaatg atgagcactt ttaaagttct      2650
gctatgtggc gcggtattat cccgtattga cgccgggcaa gagcaactcg      2700
gtcgccgcat acactattct cagaatgact tggttgagta ctcaccagtc      2750
acagaaaagc atcttacgga tggcatgaca gtaagagaat tatgcagtgc      2800
tgccataacc atgagtgata acactgcggc caacttactt ctgacaacga      2850
tcggaggacc gaaggagcta accgcttttt tgcacaacat gggggatcat      2900
gtaactcgcc ttgatcgttg ggaaccggag ctgaatgaag ccataccaaa      2950
cgacgagcgt gacaccacga tgcctgtagc aatggcaaca acgttgcgca      3000
aactattaac tggcgaacta cttactctag cttcccggca acaattaata      3050
gactggatgg aggcggataa agttgcagga ccacttctgc gctcggccct      3100
tccggctggc tggtttattg ctgataaatc tggagccggt gagcgtgggt      3150
ctcgcggtat cattgcagca ctggggccag atggtaagcc ctcccgtatc      3200
gtagttatct acacgacggg gagtcaggca actatggatg aacgaaatag      3250
acagatcgct gagataggtg cctcactgat taagcattgg taactgtcag      3300
accaagttta ctcatatata cttagattg atttaaaact tcattttaa       3350
tttaaaagga tctaggtgaa gatcctttt gataatctca tgaccaaaat       3400
cccttaacgt gagttttcgt tccactgagc gtcagacccc gtagaaaaga      3450
tcaaaggatc ttcttgagat cctttttttc tgcgcgtaat ctgctgcttg      3500
caaacaaaaa aaccaccgct accagcggtg gtttgtttgc cggatcaaga      3550
gctaccaact cttttccga aggtaactgg cttcagcaga gcgcagatac       3600
caaatactgt tcttctagtg tagccgtagt taggccacca cttcaagaac      3650
tctgtagcac cgcctacata cctcgctctg ctaatcctgt taccagtggc      3700
tgctgccagt ggcgataagt cgtgtcttac cgggttggac tcaagacgat      3750
agttaccgga taaggcgcag cggtcgggct gaacggggg ttcgtgcaca       3800
cagcccagct tggagcgaac gacctacacc gaactgagat acctacagcg      3850
tgagctatga gaaagcgcca cgcttcccga agggagaaag gcggacaggt      3900
atccggtaag cggcagggtc ggaacaggag agcgcacgag ggagcttcca      3950
gggggaaacg cctggtatct ttatagtcct gtcgggtttc gccacctctg      4000
```

-continued

```
acttgagcgt cgattttgt gatgctcgtc aggggggcgg agcctatgga        4050
aaaacgccag caacgcggcc tttttacggt tcctggcctt ttgctggcct        4100
tttgctcaca tggctcgaca                                        4120
```

```
<210> SEQ ID NO 3
<211> LENGTH: 20
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 3
cagaagttgg tcgtgaggca                                        20

<210> SEQ ID NO 4
<211> LENGTH: 20
<212> TYPE: DNA
<213> ORGANISM: Artificial Sequence
<220> FEATURE:
<221> NAME/KEY: primer_bind
<223> OTHER INFORMATION: PCR primer

<400> SEQUENCE: 4
gcctttcacc agccaagcaa                                        20

<210> SEQ ID NO 5
<211> LENGTH: 12
<212> TYPE: DNA
<213> ORGANISM: Artificial Sequence
<220> FEATURE:
<221> NAME/KEY: protein_bind
<223> OTHER INFORMATION: Furin cleavage site

<400> SEQUENCE: 5
cgtcaacgtc gt                                                12
```

GLP-1 GENE DELIVERY FOR THE TREATMENT OF TYPE 2 DIABETES

FIELD OF THE INVENTION

This invention relates to compositions and methods of use thereof to normalize the blood glucose levels of patients with type 2 diabetes. More particularly, the invention relates to a composition and method for the delivery of the GLP-1 gene, both in vitro and in vivo, for the treatment of type 2 diabetes. It relates particularly to a plasmid comprising a chicken β actin promoter and enhancer; a modified GLP-1 (7-37) cDNA (pβGLP1), carrying a furin cleavage site, which is constructed and delivered into a cell for the expression of active GLP-1. The invention also encompasses transfecting compositions comprising a complex of a plasmid containing a modified GLP-1 (7-37) cDNA (pβGLP1) and poly(ethylenimine) (PEI) (for in vitro gene delivery) or PAGA (for in vivo gene delivery).

BACKGROUND OF INVENTION

Type 2 diabetes is characterized by hyperglycemia, insulin resistance, absolute or relative insulin deficiency, hyperglucagonemia, and increased hepatic glucose production. Although many treatment trials for type 2 diabetes have been held, there is still no definitive treatment for the disease. Insulin secretion is modulated by incretin hormones which are produced by the intestinal enteroendocrine cells and constitute one arm of the enteroinsular axis. There are two major incretins. One is glucose-dependent insulinotrophic polypepetide (GIP) and the other is glucagon like peptide-1 (GLP-1). These two incretin hormones account for 20% and 80% respectively, of the intestinal incretin effect. Holst J J: Glucagonlike peptide 1: a newly discovered gastrointestinal hormone. *Gastroenterology* 107:1848-1855, 1994 GIP, but not GLP-1, tends to lose its actions in patients with type 2 diabetes. Nauck M A, Heimesaat M M, Orskov C, Holst J J, Ebert R, Creutzfeldt W: Preserved incretin activity of glucagons-like peptide 1 [7-36 amide] but not of synthetic human gastric inhibitory polypeptide in patients with type-2 diabetes mellitus. *J Clin Invest* 91:301-307, 1993. GLP-1 was recently used for the treatment of type 2 diabetes. See U.S. Pat. Nos. 5,614,492; 5,545,618 and 6,048,724 which are incorporated herein by reference.

GLP-1, produced by intestinal L-cells, stimulates glucose induced insulin secretion and inhibits glucagon secretion. GLP-1 has two active forms, GLP-1 (7-36) amide and GLP-1 (7-37), that are products of posttranslational processing of proglucagon in mammalian intestinal cells. The active forms of GLP-1 are degradable in the plasma by the action of dipeptidyl peptidase IV. During degradation, the active form of GLP1(7-36 or 7-37) loses its N-terminal amino acid residues and results in an inactive form of GLP-1 (9-36 amide). Therefore, the active forms of GLP-1 have very short plasma half lives (about 5 minutes) and metabolic clearance rates. Fehmann H C et. al: *Endocr Rev* 16:390-410, 1995 There have been several studies on administration of GLP-1 to type 2 diabetic patients which have shown that GLP-1 effectively reduces hyperglycemia in type 2 diabetic patients. Nauck et. al. *J Clin Invest* 91:301-307, 1993; Nauck et. A1: *Diabetes Care* 21:1925-1931, 1998; and Rachman J et. al *Diabetologia* 40:205-211, 1997. However, it is very difficult to consistently deliver the active form of GLP-1 because of its short half-life. Even when using the long acting form of GLP-1, exendin-4, twice daily administration is required to maintain a normal glucose level. Szayna M, Doyle M E, Betkey J A, Holloway H W, Spencer R G, Greig N H, Egan J M: Exendin-4 decelerates food intake, weight gain, and fat deposition in Zucker rats. *Endocrinology* 141:1936-1941, 2000

Gene therapy is generally considered as a promising approach, not only for the treatment of diseases with genetic defects, but also in the development of strategies for treatment and prevention of chronic diseases such as cancer, cardiovascular disease and diabetes. However, nucleic acids, as well as other polyanionic substances are rapidly degraded by nucleases and exhibit poor cellular uptake when delivered in aqueous solutions. Since early efforts to identify methods for delivery of nucleic acids in tissue culture cells in the mid 1950's, steady progress has been made towards improving delivery of functional DNA, RNA, and antisense oligonucleotides in vitro and in vivo.

The gene carriers used so far include viral systems (retroviruses, adenoviruses, adeno-associated viruses, or herpes simplex viruses) or nonviral systems (liposomes, polymers, peptides, calcium phosphate precipitation and electroporation). Viral vectors have been shown to have high transfection efficiency when compared to non-viral vectors, but due to several drawbacks, such as targeting only dividing cells, random DNA insertion, their low capacity for carrying large sized therapeutic genes, risk of replication, and possible host immune reaction, their use in vivo is severely limited.

An ideal transfection reagent should exhibit a high level of transfection activity without the need for any mechanical or physical manipulation of cells or tissues. The reagent should be non-toxic, or minimally toxic, at the effective dose. It should also be biodegradable in order to avoid any long term adverse side effects on the treated cells. When gene carriers are used for delivery of nucleic acids in vivo, it is essential that the gene carriers themselves be nontoxic and that they degrade into non-toxic products. To minimize the toxicity of the intact gene carrier and its degradation products, the design of gene carriers needs to be based on naturally occurring metabolites.

As compared to viral gene carriers, there are several advantages to the use of non-viral based gene therapies, including their relative safety and low cost of manufacture. There are several polymeric materials currently being investigated for use as gene carriers, of which poly-L-lysine (PLL) is the most popular, but few of them are biodegradable. In general, polycationic polymers are known to be toxic and the PLL backbone is barely degraded under physiological conditions. It remains in cells and tissues and causes an undesirably high toxicity. In addition, like most cationic polymers, PLL/DNA complexes have drawbacks including precipitation as insoluble particles and the tendency to aggregate into larger complexes under physiological conditions.

In view of the foregoing, there is a need for the development of a composition and a gene therapy method for the treatment of type-2 diabetes wherein the gene carrier is soluble and biodegradable, meaning that the non-viral polymer gene carrier can break down or degrade within the body to non-toxic components after the genes have been delivered.

BRIEF SUMMARY OF THE INVENTION

The present invention provides a composition and a method for delivery of the GLP-1 gene, both in vitro and in vivo, for the treatment of type 2 diabetes. Particularly, the present invention provides a plasmid comprising a chicken β actin promoter and enhancer; a modified GLP-1 (7-37) cDNA (pβGLP1) carrying a furin cleavage site. The invention also encompasses transfecting compositions comprising a complex of a plasmid containing a modified GLP-1 (7-37) cDNA (pβGLP1) and poly(ethylenimine) (PEI) (for in vitro gene delivery) or PAGA (for in vivo gene delivery), at a proper weight ratio. Particularly, the weight ratio of DNA to the cationic biodegradable gene carrier is preferably within a range 1:0.85 to 1:2.90. For DNA/PAGA, the ratio is preferably with the range of 1:0.82 to 1:2.46 and for DNA/PEI, the ratio is preferably with the range of 1:0.676 to 1:2.704 for (DNA/PEI).

This invention also provides for a method of transfecting a cell with the GLP-1 gene comprising the steps of:
(a) providing a composition comprising effective amounts of complexes of a plasmid containing a modified GLP-1 (7-37) cDNA (pβGLP1) and a polycationic gene carrier at a proper weight ratio;
(b) contacting the cell with an effective amount of the composition such that the cell internalizes the GLP-1 gene; and
(c) culturing the cell with the internalized DNA under conditions favorable for the growth thereof.

This invention further provides for a method of normalizing the blood glucose levels of an animal with type 2 diabetes, comprising the steps of:
(a) providing a composition comprising effective amounts of complexes of a plasmid containing a modified GLP-1 (7-37) cDNA (pβGLP1) and poly[α-(4-aminobutyl)-L-glycolic acid] (PAGA) at a proper charge ratio,
(b) administering to the animal to be treated an effective amount of the composition such that the cell internalizes the GLP-1 gene.

DETAILED DESCRIPTION OF THE INVENTION

Before the present composition and method for treatment of type-2 diabetes are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. In describing and claiming the present invention, the following terminology will be used in accordance with the definitions set forth below.

"Transfecting" or "transfection" shall mean transport of nucleic acids from the environment external to a cell to the internal cellular environment, with particular reference to the cytoplasm and/or cell nucleus. Without being bound by any particular theory, it is understood that nucleic acids may be delivered to cells either after being encapsulated within or adhering to one or more cationic lipid/nucleic acid complexes or entrained therewith. Particular transfecting instances deliver a nucleic acid to a cell nucleus. Nucleic acids include both DNA and RNA as well as synthetic congeners thereof. Such nucleic acids include as well as protein producing nucleotides, on and off and rate regulatory nucleotides that control protein, peptide, and nucleic acid production. In particular, but nonlimiting, they can be genomic DNA, cDNA, mRNA, tRNA, rRNA, hybrid sequences or synthetic or semi-synthetic sequences, and of natural or artificial origin. In addition, the nucleic acid can be variable in size, ranging from oligonucleotides to chromosomes. They may be obtained by any technique known to a person skilled in the art.

As used herein, the term "biodegadable" or "biodegradation" is defined as the conversion of materials into less complex intermediates or end products by solubilization hydrolysis, or by the action of biologically formed entities which can be enzymes and other products of the organism.

As used herein, "effective amount" means an amount of a nucleic acid or bioactive agent that is sufficient to provide the desired local or systemic effect and performance at a reasonable risk/benefit ratio as would attend any medical treatment.

As used herein, "administering", and similar terms means delivering the composition to the individual being treated such that the composition is capable of being circulated systemically to where the composition binds to a target cell and is taken up by endocytosis. Thus, the composition is preferably administered to the individual systemically, typically by subcutaneous, intramuscular, intravenous, or intraperitoneal administration. Injectables for such use can be prepared in conventional forms, either as a liquid solution or suspension, that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like.

According to the invention there is provided a plasmid suitable for GLP-1 eukaryotic expression, consisting essentially of: an expression facilitating sequence derived from chicken β-actin promoter and enhancer; an expression sequence comprising ATG(start codon) followed by a sequence SEQ ID NO: 5(CGTCAACGTCGT) coding for a furin cleavage site(FCS) and a sequence coding for the active form of GLP-1(7-37) that are operably linked to said expression facilitating sequence. Optionally, the plasmid may contain a non-mammalian origin of replication; and a sequence operably encoding a selectable marker.

One important aspect of the present invention relates to the addition of the furin cleavage site between the start codon and the GLP-1(7-37) gene. It is common knowledge that all gene expression requires a start codon which encodes methionine at the N terminial of a protein. Many active peptides such as GLP-1 are products of post-translation processes in vivo. If the N terminal amino acid of GLP-1 (methionine) produced from the plamid is not cleaved, it will block the activity of the first two amino acids of GLP-1 which are the receptor binding domain, which in turn makes the GLP-1 lose its biological activity completely. In order to construct a plasmid that can express high levels of active forms of GLP-1, a furin cleavage site(FCS) is introduced between the start codon and the GLP-1(7-37)sequence. Furin is a type I transmembrane protein composed of a signal peptide, a propeptide terminating in an endoproteolytic cleaveage site comprised of a cluster of basic residues, a subtilisin-like catalytic domain, a middle domain, and a cysteine-rich domain followed by C-terminal transmembrane anchor and a cytosolic tail. Therefore, when the GLP-1 produced from the plasmid constructs, according to the present invention, are secreted from the cells, the N terminal methionine-FCS of the expression product will be cleaved by the furin in the Golgi apparatus of the cells. One benefit of choosing FCS is that furin is widely distributed in most cell types, so that the plasmid constructs of the present invention can efficiently express active GLP-1 in almost any type of cell in the body. Although the plasmid constructs of the present invention are disclosed for in vivo gene delivery of active GLP-1, the usage of FCS is applicable to gene delivery of any peptide whose activity requires cleavage of the N-terminal methionine of the expression product and they intended to be within the scope of the invention.

In one embodiment of the present invention, the plasmid may possess the functional characteristics of the plasmid comprising a nucleotide sequence represented by SEQ ID NO:1. One example of the plasmid of the present invention has a nucleotide sequence represented by SEQ ID NO:2.

In another embodiment, the plasmid consisting essentially of: an expression facilitating sequence derived from chicken β-actin promoter and enhancer; an expression sequence comprising ATG(start codon) folloowed by a sequence SEQ ID NO: 5(CGTCAACGTCGT) coding for a furin cleavage site(FCS) and a sequence coding for the active form of GLP-1(7-37) or derivatives thereof that are operably linked to said expression facilitating sequence.

In another embodiment, the invention provides a host cell transformed by any of the above plasmids.

In still another embodiment, the invention provides a method for producing any of the above plasmids, comprising the steps of: growing bacterial cells containing the plasmid; and recovering the plasmid from the bacterial cells.

In an additional embodiment, the invention provides a pharmaceutical composition comprising the plasmid in combination with a pharmaceutically acceptable vehicle. The plasmid may be complexed to a biodegradable cationic polymeric gene carrier The invention also provides a eukaryotic expression vector for the expression of a DNA sequence in a human tissue, consisting essentially of: an expression facilitating sequence derived from chicken β-actin promoter and enhancer; an expression sequence comprising ATG(start codon) folloowed by a sequence SEQ ID NO: 5(CGTCAACGTCGT) coding for a furin cleavage site(FCS) and a sequence coding for the active form of a bioactive peptide that are operably linked to said expression facilitating sequence, and a sequence containing a transcriptional termination and a polyadenylation signal; and a selectable marker; wherein the vector is capable of replicating in prokaryotes.

In another embodiment, the invention provides a method of gene therapy, the improvement comprising administering any of the above plasmids directly into a cell resulting in the local secretion of active GLP-1, active GLP-1 derivatives or other peptides.

It will be readily apparent to one skilled in the art that various substitutions and modifications may be made to the invention disclosed herein without departing from the scope and spirit of the invention.

This approach differs from previous methods in which cells are collected, propagated in vitro, modified and selected and then re-injected in vivo. Limitations of these latter approaches include, 1) the need to establish a cell line from each experimental subject to avoid tissue rejection, 2) concerns about alteration of the phenotype of cells propagated in tissue culture, 3) outgrowth of aberrant transformed cells, and 4) the time and effort required. In the present method, genes are directly transferred into an animal with type-2 diabetes where the cells take up and express the gene. DNA expression is facilitated by introducing the DNA complexed with a cationic biodegradable gene carrier. The gene carrier facilitates entry of the DNA into those cells thus providing for intracellular access to the DNA/gene carrier complex. Delivery of DNA to patients in a drug-like manner is thus facilitated.

Classical pharmacological studies of drug distribution, half life, metabolism, and excretion are not entirely relevant to in vivo gene injection and expression. However, the fate of the plasmid and detection of the gene product (GLP-1) are relevant to the development of this agent. Therefore, as part of the measurement of the efficacy of this study, successful gene transfer and expression is evaluated by molecular and immunological analyses. The following parameters are measured to evaluate the transfection and expression of active GLP-1(7-37): 1) the presence of mRNA which encodes the Met-FCS-GLP-1 from the plasmid is assessed by RT-PCR amplification of cells obtained after transfection, 2) secretion of active GLP-1 from the cells transfected with the plasmid in vitro is measured by enzyme linked immunosorbent assay(ELISA), 3) measurement of insulin secretion of co-cultured islets with GLP-1 plamid transfected cells, and 4)serum glucose levels are measured pre-treatment and after the start of therapy.

The plasmid suitable for GLP-1 expression is a eukaryotic expression vector that codes for Met-FCS-GLP-1(7-37). A process for the production of this plasmid has been developed using E. coli(JM109). The process is scaleable and is a combination of highly reproducible unit operations (fermentation, cell lysis, precipitation, size exclusion chromatography, formulation and fill). The advantages over existing methods include scalability, improved plasmid purity and the elimination of undesirable process additives such as toxic solvents and animal derived enzymes. One skilled in the art will readily appreciate that the GLP-1 plasmid described herein is representative of a preferred embodiment that is exemplary and not intended to be a limitation on the scope of the invention Any eukaryotic expression vector that is adapted to carry out the objectives and obtain the ends and advantages mentioned as well as those inherent herein is encompassed within the spirit of the invention. Accordingly, the plasmids of the present invention are assembled out of components comprising a gene encoding an active peptide such as GLP-1, origins, promoters, polyadenylation signals, and furin cleavage sites(FCS).

Figure 1:
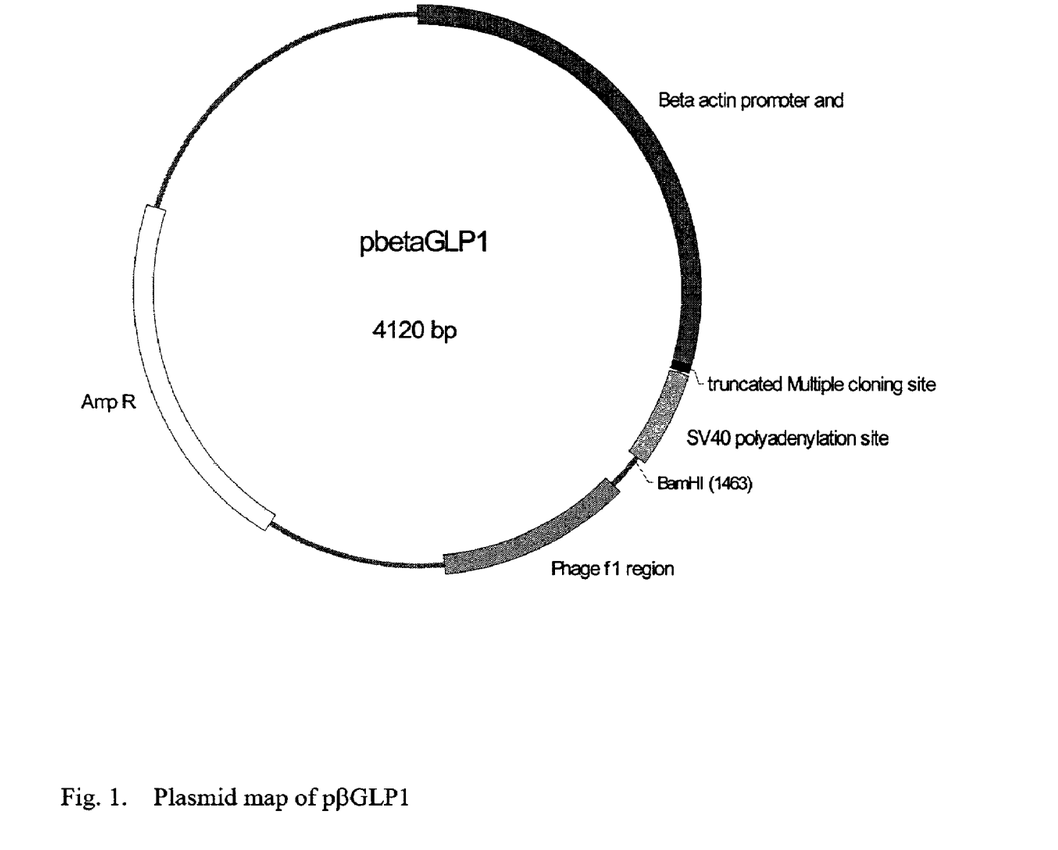
FIG. 1 is a schematic representation of plasmid pβGLP1 carrying a modified GLP-1 (7-37) cDNA sequence and a furin cleavage site.

The pβGLP-1 plasmid of the present invention is diagrammed in FIG. 1, and the nucleotide sequence of the coding strand of the plasmid is given as SEQ ID NO:2. This is a high copy number plasmid that was constructed using isolated segments of synthesized cDNA of GLP-1(3-37, using standard molecular genetic techniques and commercially available enzymes. The backbone plasmid DNA is derived from pCI (Promega Inc.), a commercially available vector widely used in molecular biology laboratories.

Development of a safe and efficient gene delivery carrier is an important factor to the success of gene therapy. Preferably, the cationic biodegradable polymeric gene carrier used in the present invention can spontaneously form discrete nanometer-sized particles with a nucleic acid, which can promote more efficient gene transfection into mammalian cells and show reduced cell toxicity. The biodegradable gene carrier, such as PAGA, is readily susceptible to metabolic degradation after incorporation into animal cells. Moreover, the polymeric gene carrier can form an aqueous micellar solution which is particularly useful for the systemic delivery of genes. PAGA is disclosed in U.S. Pat. No. 6,217,912, hereby fully incorporated by reference.

The present invention further provides transfection formulations, comprising a biodegradable cationic polymeric gene carrier complexed with an expressive gene vector carrying the GLP-1 gene, in the proper weight ratio (positive charge of the gene carrier/negative charge of the nucleic acid), that is optimally effective for both in vivo and in vitro transfection. Preferably, the biodegradable gene carrier is PAGA and the gene vector is pβGLP1. Particularly, the weight ratio of DNA to the cationic biodegradable gene carrier is preferably within a range 1:0.85 to 1:2.90. For DNA/PAGA, the ratio is preferably with the range of 1:0.82 to 1:2.46 and for DNA/PEI, the ratio is preferably with the range of 1:0.676 to 1:2.704 for (DNA/PEI).

The gene carrier of the present invention can also be conjugated, either directly or via spacer molecules, with targeting ligands. The targeting ligands conjugated to the gene carrier direct the gene carrier-nucleic acid/drug complex to bind to specific target cells and penetrate into such cells. The targeting ligand can also be an intracellular targeting element, enabling the transfer of the nucleic acid/drug to be guided towards certain favored cellular compartments (mitochondria, nucleus, and the like).

An advantage of the present invention is that it provides an efficient transfecting composition for delivery of a GLP-1 gene into a cell wherein the particle size and charge density are easily controlled. Control of particle size is crucial for optimization of a gene delivery system because the particle size often governs the transfection efficiency, cytotoxicity, and tissue targeting in vivo. In general, in order to enable its effective penetration into tissue, the size of a gene delivery particle should not exceed the size of a virus. In a preferred embodiment of the invention, the particle sizes will range from about 80 to 200 nm depending on the cationic copolymer composition and the mixing ratio of the components. It is known that particles, nanospheres, and microspheres of different sizes, when injected, accumulate in different organs of the body depending on the size of the particles injected. For example, after systemic administration, particles of less than 150 nm diameter can pass through the sinusoidal fenestrations of the liver endothelium and become localized in the spleen, and bone marrow. Intravenous, intra-arterial, or intraperitoneal injection of particles approximately 0.1 to 2.0 μm diameter leads to rapid clearance of the particles from the blood stream by macrophages of the reticuloendothelial system.

It is believed that the presently claimed composition is effective in delivering the GLP-1 gene by endocytosis. The cationic polymeric gene carrier may further comprises a targeting moiety is selected from the group consisting of transferring, asialoglycoprotein, antibodies, antibody fragments, low density lipoproteins, interleukins, GM-CSF, G-CSF, M-CSF, stem cell factors, erythropoietin, epidermal growth factor (EGF), insulin, asialoorosomucoid, mannose-6-phosphate, mannose, Lewis$^x$ and sialyl Lewis$^x$, N-acetyl-lactosamine, galactose, lactose, and thrombomodulin, fusogenic agents such as polymixin B and hemaglutinin HA2, lysosomotrophic agents, and nucleus localization signals (NLS). Nucleic acid transfer to targeted cells can be carried out by matching a cell having a selected receptor thereof with a selected targeting moiety. The present invention therefore provides methods for treating type 2 diabetes by in vivo delivery of an expressive gene vector which provides a desirable amount of GLP-1 protein during a sustained period of time.

The biodegradable transfecting composition of the present invention, as described herein, exhibits improved cellular binding and uptake characteristics toward the GLP-1 gene to be delivered. As such, the present invention overcomes the problems as set forth above. For example, the biodegradable gene carrier of the present invention, such as PAGA, is easily hydrolyzed or degraded into low molecular weight components which will be easily eliminated from the body. In addition, the degradation products are small, nontoxic molecules that are subject to renal excretion and are inert during the period required for gene expression. Moreover, cells transfected with the plasmid of the present invention, namely, pβGLP-1(3-37), can produce the most potent form of natural GLP-1 peptide. There are two characteristics in the plasmid constructs of the present invention that afford the capability of producing the most potent form of natural GLP-1 peptide. First of all, there is a furin cleavage site between the start codon and the GLP-1 gene, thus furin cleaves the first amino acid, methionine, which is encoded by the start codon. Therefore, the cleavage of methionine preserved the function of the next two amino acids which is the GLP-1 receptor binding domain and which is essential for GLP-1 activity. Secondly, the replacement of chicken β actin promotor of the CMV promotor provides the plamids the capability of expressing higher amounts of the active GLP-peptide in cells because chicken β actin promotor is a more potent promotor than the CMV promotor.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE 1

Construction of Plasmid Vector

This example illustrates the construction of the plasmid which expresses GLP-1 (FIG. 1.). In this plasmid, GLP-1 expression was driven by chicken β actin promoter and enhancer. GLP-1 (7-37) gene was synthesized using a DNA synthesizer. The start codon encodes methionine. If the N-terminal amino acid of the produced GLP-1 is methionine, it will not be an active form, because the first two amino acids of GLP-1 are the receptor binding domain. A furin recognition site (ArgGlyArgArg: SEQ ID NO: 5 CGT-CAACGTCGT) was inserted into the synthesized GLP-1 (7-37) gene just after the start codon. When the produced GLP-1 is secreted from the cell, the methionine is cleaved by the furin in the Golgi apparatus. To replace the promoter part (chicken β actin promoter and CMV promoter),chicken β-actin promoter and enhancer were isolated from pEBAct-NII by digestion with BglII and XbaI. The pEBActNII was provided by Dr. Kaneda (Osaka University). The CMV promoter of pCI (Promega Inc.) was also disgested with BglII and XbaI. Both digested DNA fragments were confirmed by their size using a gel electrophoresis. And then the DNA fragments in agarose gel were extracted using Gel Extraction Kit (Quiagen Inc.) The gel extraction was performed following their prescribed procedure. The two extracted fragments were ligated using T4 DNA ligsae (Promega Inc.) under 17° C. for 16 hours, and we named our final plasmid pβ. The synthesized GLP-1 (7-37) was treated with KpnI and XbaI and inserted into the KpnI and XbaI sites of pβ plasmid. The gel extraction and ligation methods are same as described above. The resulting pβGLP1 was amplified in *E. coli* JM109 (Promega) and purified by an alkaline lysis method using the Maxi Prep Kit (Qiagen). The purity of the plasmid was confirmed by absorbance at 260 nm and 280 nm and the quantity was determined by absorbance at 260 nm. The constructed plasmid was confirmed by DNA sequencing.

EXAMPLE 2

Synthesis of PAGA and Formation of PAGA/DNA Complex

This example illustrates the preparation of a gene delivery composition, according to the present invention.

PAGA was synthesized as previously described in U.S. Pat. No. 6,217,912, hereby incorporated by reference. Briefly, CBZ-L-oxylysine was synthesized from CBZ-L-lysine. CBZ-L-oxylysine was polymerized by a melting condensation reaction at 150° C. under a vacuum of $10^{-4}$ Torr for 5 days. The polymer was dissolved with chloroform and precipitated with methanol. The dried polymer was dissolved with DMF containing a palladium activated carbon catalyst. 85% formic acid was added as a proton donor. After 15 hours at room temperature, the polymer solution was isolated from the catalyst by addition of 2 N HCl and the polymer was precipitated with acetone. PAGA was stored at −70° C. until use.

The DNA/carrier complexes were prepared by self assembly. PEI (25,000 Da) and PAGA were dissolved in PBS (pH 7.3). Ten times diluted carrier solution was slowly added into the prepared DNA plasmid and left for 30 minutes to allow for formation of complexes. The formation of the complexes pβGLP1/PEI and pβGLP1/PAGA was routinely monitored by 1.0% agarose gel electrophoresis.

Stable complexes were formed with PAGA and the aqueous plasmid DNA solution based on the fact that no precipitation or aggregation was observed at wide concentration ranges of the complexes in the PBS buffer. Complex formation of the plasmid DNA and the cationic copolymer was tested by agarose gel. The results show that complete neutralization was achieved from the weight ratio of DNA to the cationic polymer is within a range of 1:0.82 to 1:2.46.

EXAMPLE 3

Expression of GLP-1 mRNA in Transfected HepG2 Cells

This example illustrates the expression of GLP-1 mRNA in transfected HepG2 cells. To analyze the expression of the gene, RT-PCR was carried out on the pβGLP1/PEI complex that was transfected into HepG2 cells used to evaluate the expression of GLP-1

HepG2 cells were maintained in MEM supplemented with 10% FBS in a 5% $CO_2$ incubator. For the transfection studies, the cells were seeded at a density of $2.25 \times 10^5$ cells/6 well culture plates and incubated for 24 hours before the addition of the pβGLP1/PEI complex. The pβGLP1/PEI complexes were prepared by mixing plasmid and PEI at an N/P ratio of 1:5 (the weight ratio was 1:0.676) in serum free MEM medium and then incubated for 30 minutes at room temperature. The cells were washed twice with PBS, and then 2 mL of fresh serum-free MEM media was added. The pβGLP1/PEI complex was added to each well. The cells were incubated for 4 hours at 37° C. in a 5% $CO_2$ incubator. After 4 hours, the transfection mixtures were removed and 2 mL of fresh MEM containing FBS was added. The cells were incubated for an additional 24 hrs at 37° C. We collected the media that was treated with dipeptidyl peptidase IV inhibitor. Then a GLP-1 assay (Linco Inc.) was carried out following the suppliers manual The transfected cells were washed twice with PBS, and total RNA was harvested by acid-guanidium thiocyanate-phenol-chloroform extraction, using RNAwiz (Ambion, Austin, Tex.). The concentration of RNA was measured by the absorbance at 260 nm, and the integrity of RNA was confirmed by formaldehyde-formamide denatured agarose gel electrophoresis. Two micrograms of total RNAs were hybridized to the backward primer and reverse transcribed using AMV reverse transcriptase (Promega, Madion, Wis. The reverse transcribed samples were amplified by polymerase chain reaction (PCR), using Taq polymerase (Promega, Madison, Wis.). The sequences of the specific oligonucleotide primers were as follows: GLP-1 forward primer, SEQ ID NO: 3 5'-CAGAAGTTGGTCGTGAG-GCA-3'; GLP-1 backward primer, SEQ ID NO: 4 5'-GC-CTTTCACCAGCCAAGCAA-3'. The PCR reaction was performed in 25 cycles at 94° C. for 30 seconds, 55° C. for 30 seconds, 72° C. for 1 minute, followed by an extension of 10 minutes at 72° C. The PCR products were analyzed in 2% agrose gel electrophoresis. The sizes of the expected products were 110 bp for GLP-1.

Figure 2A:
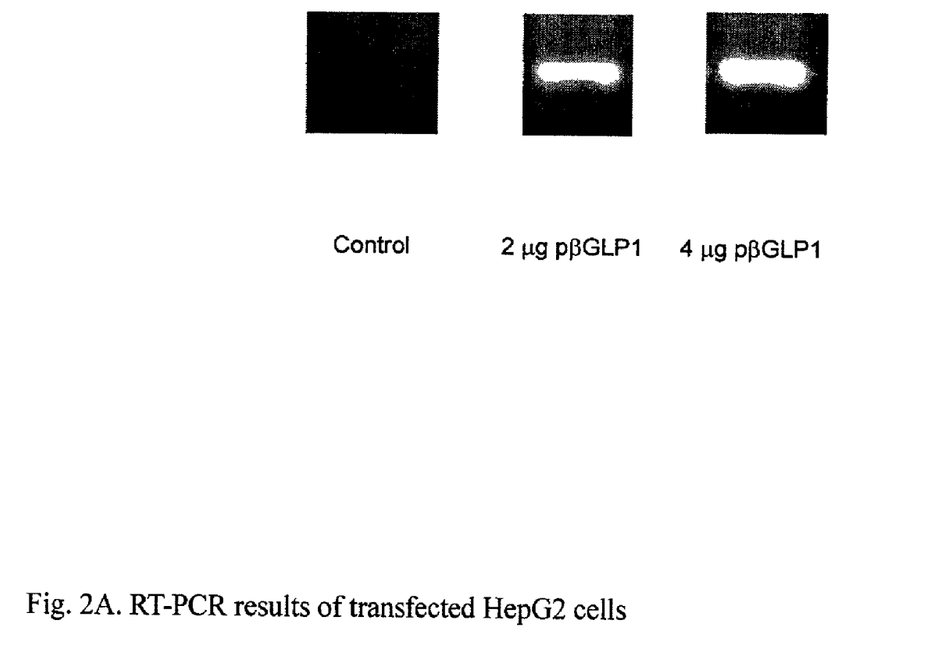
FIG. 2 shows the RT-PCR assay of the production of GLP-1 in HepG2 cells transfected by the transfection composition containing pβGLP1/gene carrier complexes.

As a result, the GLP-1 mRNA was detected in the pβGLP1 plasmid transfected cells. (FIG. 2A). The transfected HepG2 cells expressed GLP-1 mRNA in a dose dependent manner. Therefore, this result suggests that the detected mRNA was expressed by the exogenous transferred pβGLP1 plasmid, not by the endogenous GLP-1 gene. Also, the expression level can be controlled by the dose of pβGLP1 administration.

EXAMPLE 4

ELISA Detection of GLP-1 in Transfected HepG2 Cells

This example illustrates the expression of GLP-1 in transfected HepG2 cells. To detect the expression of the active GLP-1 peptide, ELISA was carried out on the pβGLP1/PAGA complex that was transfected into HepG2 cells used to evaluate the production of active GLP-1.

Figure 2B:
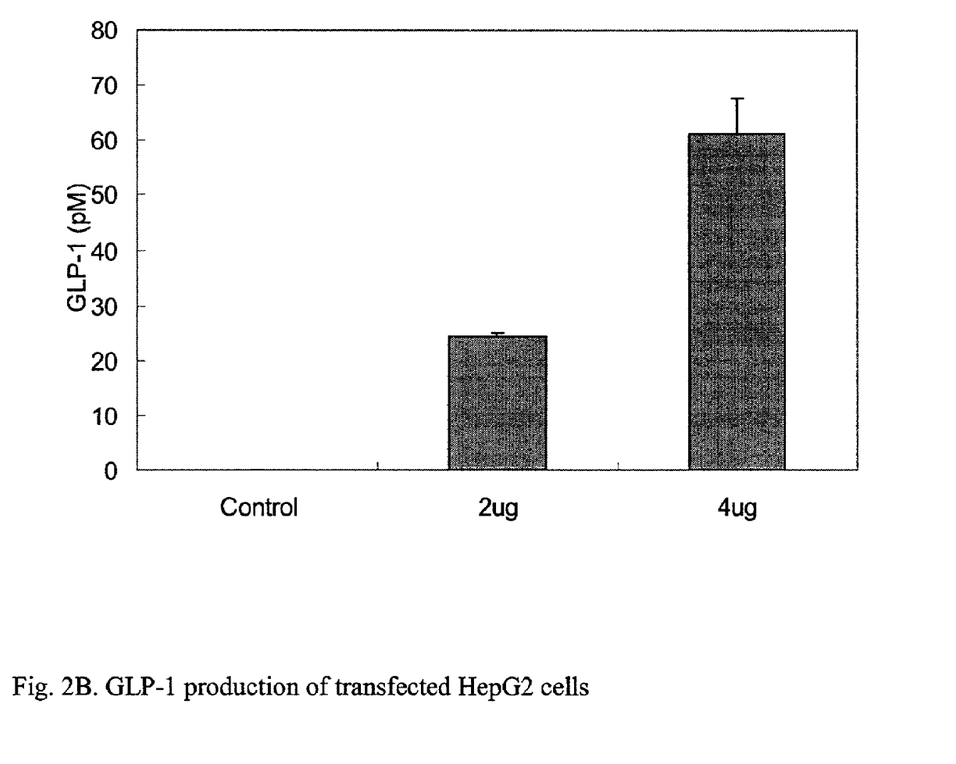

HepG2 cells were cultured and transfected with the plasmid of the present invention as described in Example 3. In order to confirm that the expressed GLP-1 should be secreted and active for therapeutic purpose, ELISA assays for the active form of GLP-1 were performed 48 hours after transfection, using the active GLP-1 ELISA kid(Linco, Inc). As illustrated in FIG. 2B, the active form of GLP-1 was detected in the cell culture media by an ELISA assay, suggesting that the expressed GLP-1 by pβGLP1 was secreted into the cell culture media. The GLP-1 production of the transfected HepG2 cells was 24.5±0.5 pM/24 hrs (2 µg of pβGLP1 transfected) and 61.3±6.2 pM/24 hrs (4 µg of pβGLP1 transfected). However, there was no production of GLP-1 from the negative control.

EXAMPLE 5

Co-Culture Rat Islets with pβGLP1 Transfected HepG2 Cells

The example illustrates the effect of the secreted GLP-1 on the secretion of insulin from rat islets.

Islets of Langerhans were isolated from male Sprague-Dowley rat pancreas, by a collagenase digestion technique and discontinuous Ficoll density gradient centrifugation. Briefly, the pancreas was removed after swelling caused by collagenase solution injection (Type V, Sigma, 10-15 ml/pancreas, 1 mg/ml in HBSS) through the common bile duct, and incubated for 15 min at 37° C. The digested fragments of the pancreas were collected and washed with HBSS. Finally, the acinar cells and islets were separated by Ficoll density gradient centrifugation (11%, 20%, 23%, and 27% in HBSS). The islet rich layer was collected and washed with HBSS, and the islets were suspended in RPMI-1640 medium with 10% FBS and incubated at 37° C. under humidified conditions with 5% $CO_2$. On average, 500-700 islets were isolated from a rat pancreas. For the co-culture study, the isolated islets were sub-cultured for 24-48 hours.

For transfection, HepG2 cells cultured in MEM supplemented with 10% FBS were used. The cells were seeded at a density of $5 \times 10^5$/well in a 6 well plate with 1.5 mL medium. After 24 hours incubation, the culture medium was changed to FBS free fresh medium and loaded with pβGLP1/PEI complexes (PEI/DNA N/P ratio 5 the weight ration of DNA/PEI is 1:0.676, 4 µg DNA/well) followed by 4 hours incubation at 37° C. with 5% $CO_2$. Then, the transfection medium was changed to fresh MEM with 10% FBS and the cells were incubated for another 48 hours before the co-culture study at 37° C. with 5% $CO_2$.

The co-culture study was performed with isolated islets and pβGLP1 transfected HepG2 cells. 30 islets with a small size distribution (mean size of 150 µm) were carefully transferred into the pβGLP1 transfected HepG2 cells culture system. The islets and HepG2 cells were separated by a physical barrier (cell culture insert). Then, the culture medium was changed to fresh RPMI-1640 medium (1.5 mL) supplemented with 10% FBS with basal and high glucose content (50 mg/dL, 300 mg/dL). After 4 h co-incubation, the insulin and GLP-1 content in the medium was measured by RIA and ELISA, respectively.

Figure 3:
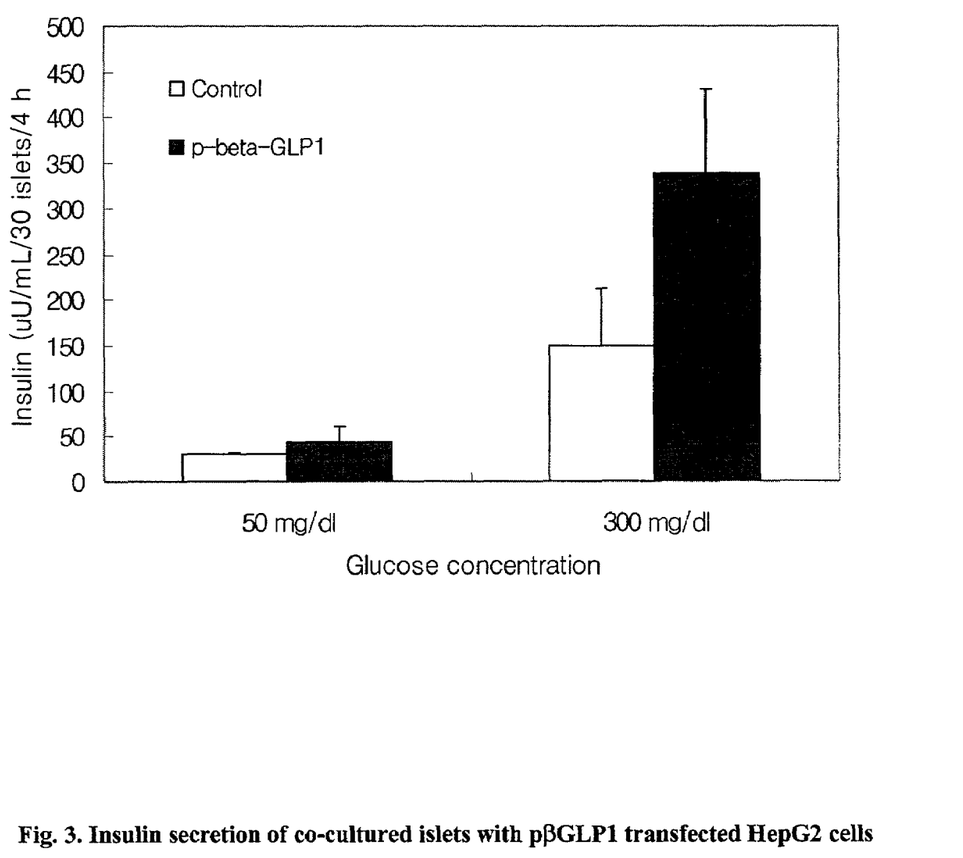
FIG. 3 shows the insulin secretion of co-cultured islets with HepG2 cells transfected by the transfection composition containing pβGLP1/gene carrier complexes.

The transfected HepG2 cells of each well produced from 3.3 pM/4 hrs to 4.6 pM/4 hrs. There was no enhancement of insulin secretion under a low glucose concentration (50 mg/dL). However, a remarkable increment of insulin secretion occurred under high glucose concentrations (300 mg/dL). (FIG. 3.)

The stimulation index was 5.1 (in the control group) and 7.9 (in the transfected group) respectively. ($p < 0.05$) These findings show that GLP-1 stimulated the secretion of insulin under high glucose conditions but did not stimulate insulin secretion under low glucose conditions.

EXAMPLE 6

Delivery of pβGLP1/PAGA Complex to Type 2 Diabetic Animals

In this example, the PAGA/pβGLP1 complex was delivered into type 2 diabetic animals in vivo.

The type 2 diabetic animal was ZDF (Zucker Diabetic Fatty) rats. These rats have homozygote leptin receptor mutations, so they seem to have similar manifestations of human type 2 diabetes. The DNA/carrier complexes were prepared by self assembly. PAGA was dissolved in distilled water. Before addition of PAGA into the DNA, the DNA was diluted in 5% glucose solution. Ten times diluted carrier solution was slowly added into the prepared DNA plasmid and left for 30 minutes to allow for formation of complexes. PAGA was injected as a control measure. (DNA/PAGA weight ratio was 1:1.23) The total volume of DNA/PAGA complex was 2.5 mL. (in 5% glucose solution) Before injection, the rats were incised in their right side neck areas under anesthesia to expose their jugular veins. The solution containing pβGLP1/PAGA complex was injected through the jugular vein. One rat was injected with 250 µg of plasmid and another was injected with 50 µg of plasmid.

Figure 4:
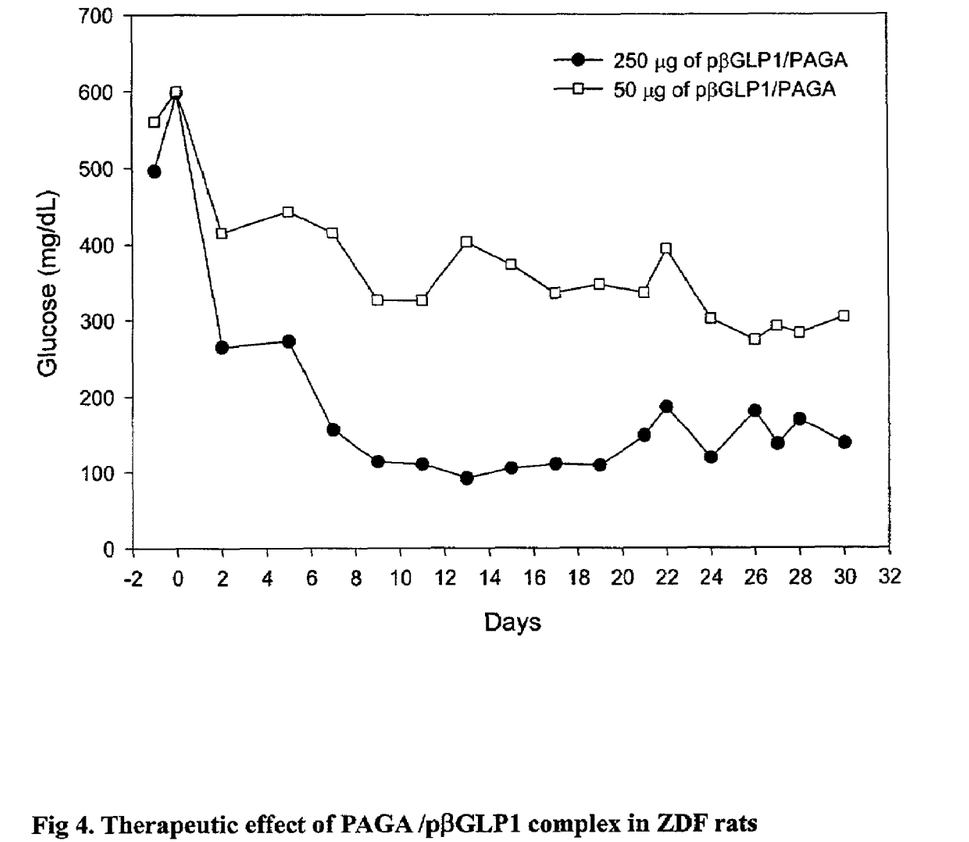
FIG. 4. illustrates the therapeutic effect of the transfection composition containing pβGLP1/PAGA complexes in Zucker Diabetic Fatty(ZDF) rats.

The blood glucose levels were checked every other day using a portable glucometer (Accucheck, Roche Inc). The blood glucose levels were normalized 7 days after injection of the pβGLP1/PAGA complex. Also, normal glucose levels were sustained for 4 weeks. The glucose levels of the treatment group were maintained at less than 150 mg/dL. (FIG. 4.)

EXAMPLE 7

Delivery of pβGLP1/Biodegradable Polymeric Gene Carrier Complex to Patients with Type 2 Diabetes In this example, the PAGA/pβGLP1 complex will be delivered into type 2 diabetic patients in vivo.

The PAGA/pβGLP1 complex prepared as in Example 6 will be injected into the peripheral vein of patients. Each patient will be injected with 20 mg of plasmid DNA. (Weight ratio of DNA/PAGA will be 1:1.23). Total volume of pβGLP1/PAGA complex solution will be 200 mL, so it will be injected 50 mL bolus I.V. every day for four days. Same amount of PAGA (24.6 mg in 200 mL, 5% glucose solution) will be injected to control group. Control and treatment group will be composed of twenty type 2 diabetics, respectively. The blood samples will be collected every three days for plasma insulin and GLP-1 levels. And blood glucose concentration will be measured four times every day. It is expected that among the patient who has the treatment of pβGLP1/PAGA complex, the blood glucose levels should be normalized about five to ten days after injection of the pβGLP1/PAGA complex. Also, normal glucose levels is expected to be sustained for at least weeks.

Thus, among the various embodiments taught there has been disclosed a composition and method for delivering the GLP-1 gene, both in vitro and in vivo, for the treatment of type 2 diabetes. It will be readily apparent to those skilled in the art that various changes and modifications of an obvious nature may be made without departing from the spirit of the invention, and all such changes and modifications are considered to fall within the scope of the invention as defined by the appended claims.

We claim:

1. A plasmid comprising the nucleotide sequence of SEQ ID NO:1.

* * * * *